United States Patent
Wang

(10) Patent No.: US 11,833,182 B2
(45) Date of Patent: Dec. 5, 2023

(54) SLEEP PRODUCT

(71) Applicant: Shaklee Corporation, Pleasanton, CA (US)

(72) Inventor: Hong Wang, Pleasanton, CA (US)

(73) Assignee: Shaklee Corporation, Pleasanton, CA (US)

( * ) Notice: Subject to any disclaimer, the term of this patent is extended or adjusted under 35 U.S.C. 154(b) by 0 days.

(21) Appl. No.: 17/398,811

(22) Filed: Aug. 10, 2021

(65) Prior Publication Data

US 2023/0049627 A1 Feb. 16, 2023

(51) Int. Cl.
| | |
|---|---|
| *A61K 36/35* | (2006.01) |
| *A61K 9/48* | (2006.01) |
| *A61K 31/198* | (2006.01) |
| *A61K 31/4045* | (2006.01) |
| *A61K 36/53* | (2006.01) |

(52) U.S. Cl.
CPC ............. *A61K 36/35* (2013.01); *A61K 9/48* (2013.01); *A61K 31/198* (2013.01); *A61K 31/4045* (2013.01); *A61K 36/53* (2013.01)

(58) Field of Classification Search
None
See application file for complete search history.

(56) References Cited

U.S. PATENT DOCUMENTS

| | | | |
|---|---|---|---|
| 5,449,683 A | 9/1995 | Wurtman | |
| 7,273,621 B2 * | 9/2007 | Ozeki | A61K 31/198 424/725 |
| 7,476,405 B2 | 1/2009 | Gardiner et al. | |
| 10,517,322 B1 | 12/2019 | Lee | |
| 2017/0020815 A1 * | 1/2017 | Gutierrez | A61K 47/18 |
| 2017/0209383 A1 | 7/2017 | Gerchenson | |
| 2018/0098962 A1 * | 4/2018 | Bromley | A61K 31/4745 |

FOREIGN PATENT DOCUMENTS

WO WO 2020/206205 10/2020

OTHER PUBLICATIONS

Attenburrow et al., "Low dose melatonin improves sleep in healthy middle-aged subjects," *Psychopharmacology*, vol. 126, pp. 179-181, Jul. 1996.
Dawson et al., "The hypothermic effect of melatonin on core body temperature: is more better?" *J. Pineal Res.*, 20(4): 192-197, May 1996.
Taavoni et al., "Valerian/lemon balm use for sleep disorders during menopause," *Complementary Therapies in Clinical Practice*, 19(4):193-196, Sep. 10, 2013.
Wurtman et al., "Improvement of sleep quality by melatonin," *The Lancet*, vol. 346, p. 1491, Dec. 2, 1995.
Zhdanova et al., "Pharmacodynamics and drug action: Sleep-inducing effects of low doses of melatonin ingested in the evening," *Clinical Pharmacology & Therapeutics*, 57(5): pp. 552-558, May 1995.
Pure Encapsulations® 2017 Professional Product List, 220 pages, Jan. 2017.
Head et al., "Nutrients and Botanicals for Treatment of Stress: Adrenal Fatigue, Neurotransmitter Imbalance, Anxiety, and Restless Sleep," *Alternative Medicine Review*, 14(2): 114-140, Jun. 2009.
International Search Report and Written Opinion issued for International Application No. PCT/US2022/030050 dated Sep. 15, 2022.
Mintel, "Power to Sleep PM" product information, Oct. 24, 2016.
Mintel, "Sleep Aid" product information, Dec. 17, 2007.
Mintel, "Natra Sleep Vegetarian Capsules" product information, Aug. 16, 2018.

\* cited by examiner

*Primary Examiner* — Susan Hoffman
(74) *Attorney, Agent, or Firm* — Klarquist Sparkman, LLP

(57) ABSTRACT

A sleep supplement composition that includes valerian extract, lemon balm extract, and L-theanine. In certain embodiments, the composition also includes melatonin.

8 Claims, No Drawings

SLEEP PRODUCT

BACKGROUND

Dietary supplements are products intended to supplement the diet. Dietary supplements can contain one or more dietary ingredients, including vitamins, minerals, herbs, amino acids, and other substances. Dietary supplements can be taken by mouth as a pill, capsule, tablet, or liquid, and can usually be labeled on the front panel as being a dietary supplement.

SUMMARY

Disclosed herein in one embodiment is a sleep supplement composition comprising 50 mg to 275 mg valerian extract, 20 mg to 140 mg lemon balm extract, and 1.0 mg to 13.0 mg L-theanine.

Also disclosed is a dosage unit comprising 50 mg to 275 mg valerian extract, 20 mg to 140 mg lemon balm extract, and 1.0 mg to 13.0 mg L-theanine, wherein the dosage unit is in the form of a softgel capsule for promoting sleep.

Further disclosed are methods for promoting sleep in an individual in need thereof, by orally administering to the individual a sleep supplement composition or dosage unit as described herein.

DETAILED DESCRIPTION

Terminology

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration" as used herein is inclusive of administration by another person to the subject or self-administration by the subject.

An "effective amount" refers to a quantity of a specified agent sufficient to achieve a desired effect in an individual.

Compositions

Disclosed herein are compositions in the form of dietary supplements useful for helping individuals, among other things, induce and maintain sleep, encourage natural sleep, improve quality of sleep, reduce time required to fall asleep, and/or achieve deep and restful sleep. The compositions include valerian extract, lemon balm extract, and L-theanine. In certain embodiments, the compositions also include melatonin. In certain embodiments, melatonin, valerian extract, lemon balm extract, and L-theanine are the only sleep inducing-active components of the compositions.

In certain embodiments, the melatonin may be present in an amount of at least 0.5, 1.0, 1.5, 2.0, 2.5 or 3 mg. In certain embodiments, the melatonin may be present in an amount of up to 1.0, 1.5, 2.0, 2.5, 3.0, 3.5, 4.0, 4.5, 5.0 or 5.5 mg. In certain embodiments, the melatonin is present in an amount of 0.5 to 5.5 mg, more particularly 1.0 to 4.0 mg.

In certain embodiments, the valerian extract may be present in an amount of at least 50, 75, 100, 125, 150, 175, 200 or 225 mg. In certain embodiments, the valerian extract may be present in an amount of up to 75, 100, 125, 150, 175, 200, 225, 250 or 275 mg. In certain embodiments, the valerian extract is present in an amount of 50 to 275 mg, more particularly 100 to 200 mg.

In certain embodiments, the lemon balm extract may be present in an amount of at least 20, 30, 40, 50, 60, 70, 80, 90 or 100 mg. In certain embodiments, the lemon balm extract may be present in an amount of up to 40, 50, 60, 70, 80, 90, 100, 110, 120, 130 or 140 mg. In certain embodiments, the lemon balm extract is present in an amount of 20 to 140 mg, more particularly, 50 to 120 mg.

In certain embodiments, the L-theanine may be present in an amount of at least 1.0, 2.0, 3.0, 4.0, 5.0, 6.0, 7.0 or 8.0 mg. In certain embodiments, the L-theanine may be present in an amount of up to 4.0, 5.0, 6.0, 7.0, 8.0, 9.0, 10.0, 11.0, 12.0 or 13.0 mg. In certain embodiments, the L-theanine is present in an amount of 1.0 to 13.0 mg, more particularly, 6.0 mg to 11.0 mg.

In certain embodiments, the combined amount of valerian extract, lemon balm extract, and L-theanine is 100 mg to 400 mg, more particularly 150 mg to 300 mg.

In certain embodiments, the valerian extract is from the root of *Valeriana officinalis*.

In certain embodiments, the lemon balm extract is from the leaf of *Melissa officinalis*.

The compositions can be formulated in pharmaceutically acceptable carriers, for example to produce nutraceuticals in the form of dietary supplement dosage forms (such as tablets or capsules), liquids (such as beverages or gels), and consumable products (such as foods or powders that are mixed with liquids).

The compositions may include at least one excipient. In certain embodiments, the excipient is an inactive substance used as a carrier for the active ingredients of the composition. Excipients can include substances that are used to bulk up formulations with very potent active ingredients, allow for convenient and accurate dosage, stabilize the active ingredients, and make the delivery system optically and/or organoleptically acceptable. Examples of pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like.

*Remington's Pharmaceutical Sciences*, by E. W. Martin, Mack Publishing Co., Easton, PA, 19th Edition (1995), describes compositions and formulations suitable for pharmaceutical delivery of one or more compositions. The use of pharmaceutically acceptable excipients does not imply that that product so made is useful only for pharmaceutical purposes. Rather it implies that the product is suitable for administration to or consumption by a subject, for example as a pharmaceutical or nutraceutical that is suitable for oral ingestion by a subject.

In general, the nature of the excipient will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid vehicles can include, for example, pharmaceutical grades of mannitol, lactose, starch, or magnesium stearate. In addition to biologically-neutral vehicles, the compositions to be administered can contain minor amounts of non-toxic auxiliary substances, such as wetting or emulsifying agents, preservatives, and pH buffering agents and the like, for example sodium acetate or sorbitan monolaurate.

The disclosed compositions can be enclosed in multiple or single dose containers. The compositions can also be provided in kits, for example, including component parts that can be assembled for use. For example, one or more of the disclosed ingredients may be provided in a lyophilized form and a suitable diluent may be provided as separated components for combination prior to use. The containers are preferably adapted for the desired mode of administration, including, but not limited to tablets, gel capsules, sustained-release capsules, and the like for oral administration.

The active components are included in the pharmaceutically acceptable carrier in an amount sufficient to exert a therapeutically useful effect in the absence of undesirable side effects on the subject treated. A therapeutically effective concentration may be determined empirically by testing the compounds in known in vitro and in vivo model systems. In some examples, a therapeutically effective amount of the component is an amount that lessens or ameliorates at least one condition for which the composition is administered. Typically, the compositions are formulated for single dosage administration. The concentration of active components in the composition will depend on absorption, inactivation, and excretion rates of the active component, the dosage schedule, and amount administered as well as other factors known to those of skill in the art.

In some examples, the active components are compounded with at least one physiologically acceptable carrier and/or excipient in a dosage unit form. The amount of active substance in those compositions or preparations is such that a suitable dosage in the range indicated is obtained. The term "dosage unit " refers to physically discrete units suitable as unitary dosages for human subjects and other mammals, each unit containing a predetermined quantity of active material calculated to produce the desired therapeutic effect, in association with a suitable pharmaceutical excipient.

The disclosed compositions may be administered as a single dose, or may be divided into a number of smaller doses to be administered at intervals of time. The compositions can be administered in a single dose delivery, by continuous delivery over an extended time period, in a repeated administration protocol (for example, by a multi-daily, daily, weekly, or monthly repeated administration protocol.

When administered orally as a suspension, these compositions are prepared according to techniques well known in the art of pharmaceutical formulation and may contain microcrystalline cellulose for imparting bulk, alginic acid or sodium alginate as a suspending agent, methylcellulose as a viscosity enhancer, and sweeteners/flavoring agents. As immediate release tablets, these compositions may contain microcrystalline cellulose, dicalcium phosphate, starch, magnesium stearate and lactose and/or other excipients, binders, extenders, disintegrants, diluents and lubricants. If oral administration is desired, the composition is typically provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active components can be incorporated with excipients and used in the form of tablets, capsules, or troches. Pharmaceutically compatible binding agents and adjuvant materials can be included as part of the composition. The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents.

When administered orally, the compositions can be administered in dosage forms for oral administration. These dosage forms include the usual solid unit dosage forms of tablets and capsules as well as liquid dosage forms such as solutions, suspensions, and elixirs. When the solid dosage forms are used, it is preferred that they be of the sustained release type so that the compounds need to be administered only once or twice daily. In some examples, an oral dosage form is administered to the individual 1, 2, 3, 4, or more times daily.

For solid compositions such as powder, pill, tablet, or capsule forms conventional non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances or excipients, such as wetting or emulsifying agents, preservatives, and pH buffering agents and the like; for example, sodium acetate or sorbitan monolaurate. Other non-limiting excipients include, nonionic solubilizers, such as cremophor, or proteins, such as human serum albumin.

In certain embodiments, there is provided a capsule comprising a fill composition, and a shell surrounding the fill. The fill composition may be any of the sleep compositions described herein. The fill composition may also include liquid vehicle ingredients as described in more detail below. Optionally, a coating may be provided around the shell.

The capsule prevents degradation of the fill composition and allows for storage for a period of several months at room temperature. The capsule is adapted for self-administration by an individual. The capsule shell dissolves or disintegrates in the digestive tract after the capsule is ingested, thereby releasing the therapeutic composition to be absorbed by the body of the individual ingesting the capsule.

Capsule shells are typically made of either animal based or plant based components that readily dissolve or disintegrate after ingestion. Animal based components may include gelatin manufactured from the collagen of animal skin and/or bone. In certain embodiments, the capsule is made of gelatin. Other suitable matrix substances such as total synthetic polymer chemicals having gelatin-like properties may be used to manufacture the capsules. Plant based components may include vegetable starch, cellulose, hypromellose (a polymer formulated from cellulose) or pullulan (polysaccharide polymer produced from tapioca starch). In some embodiments, plant based components may include carrageenan, potato starch, cassava starch, cornstarch, arrowroot or combinations thereof. The composition, manufacture, and use of capsule shells are well known in the art.

In certain embodiments, the capsule is a softgel capsule, also referred to herein. Softgel capsules are particularly suitable for containing liquid-based ingredients, such as therapeutic ingredients dissolved, dispersed, and/or suspended in a liquid vehicle. Softgel capsules also possess particular advantages for substances which require total protection from air and light. For example, the softgel capsule can block a significant amount (e.g., at least 90%, at least 99%, or up to 100%) of UV light from transmitting therethrough.

One advantage of softgel capsules is the improved rate and extent of absorption, and the reduced variability per dosage, particularly for water soluble pharmaceutical agents. Another advantage of softgel capsules is that they are substantially easier to swallow than, for example, tablets or hard-shell capsules. Yet another advantage is the absence of poor taste, aftertaste, sharp edges or other sensory problems associated with alternatives such as tablets or hard-shell capsules. Another advantage is an improved patient compliance compared to tablets and hard-shell capsules.

Another advantage is the ease and convenience of orally administering pharmaceuticals that have to be formulated in liquid dosage form. Yet another advantage is the improved ability to control the exact amount of a liquid therapeutic agent compared to a solid or powder form. Another advantage is their resistance to tampering and/or altering the dosage after formulation and before administration. Yet another advantage is that the active therapeutic agent is hermetically sealed.

Another advantage is the improved homogeneity of the formulation compared to a tablet, granules or powder formulation. Yet another advantage is the enhanced stability of the therapeutic agent in the softgel capsule. Another advantage is the ease of storage and increased shelf life of the softgel capsule compared to hard-shell capsules. Yet another advantage is the rapid disintegration of the softgel capsule upon administration leading to enhanced rate of absorption of the therapeutic agent, and thereby, an improved rate of therapeutic effect compared to, for example, tablets. Another advantage is the substantially decreased plasma variability of the therapeutic, thereby leading to an enhanced level of bioavailability upon administration compared to tablets and hard-shell capsules.

The shell of a softgel capsule is typically made of animal-based and/or plant-based components combined with a plasticizer such as glycerin and a solvent such as water. In some embodiments, plant based components such as cellulose, hypromellose, vegetable starch, tapioca starch, carrageenan, potato starch, cassava starch, cornstarch, arrowroot or combinations thereof may be used in place of gelatin to make vegetarian softgel capsules. Other animal based or plant based components with properties similar to gelatin or starch that are suitable for polymerization or activated crosslinking may also be used. Softgel capsule shells are typically made and filled with therapeutic formulations in continuous processes that are known in the art.

The term "plasticizer" refers to a substance that is added to the gelatin or starch to form the softgel capsule. Plasticizers may include glycerin, sorbitol, propylene glycol, other suitable polyols, or combinations thereof. The amount of plasticizer can be adjusted to arrive at softgel shells with the desired level of softness and flexibility. Some embodiments may include from about 30 to about 50% by weight the plant-based component; at least 18% by weight, and preferably up to about 40% by weight, of a plasticizer; and from about 20 to about 50% by weight water. These formulations, when formed into capsules and dried, will result in softgel capsules containing from about 40 to about 75% by weight plant-based component; from about 18% to about 40% by weight plasticizer; and from about 5 to about 15% by weight water. The softgel shells may be prepared by combining appropriate amounts of plant-based component, water, plasticizer, and any optional components in a suitable vessel and agitating and/or stirring while heating until a uniform solution is obtained.

In some embodiments, the softgel shells include a layer or coating. The coating may include a film coating or an enteric resistant coating that allows for controlled release, delayed release or sustained release of the contents of the capsule upon administration.

The term "preservative" refers to compounds which are used to prevent the growth of bacteria, fungi, mold and other microbes. They are used for their individual antibacterial (destroying and inhibiting the growth of bacteria), antifungal (destroying and inhibiting the growth of fungus), anti-microbial, anti-mycoplasmal, anti-viral and/or anti-prion properties. Suitable preservatives can include, but are not limited to, at least one of a benzalkonium chloride, a benzethonium chloride, a chlorohexidine, a phenol, a m-cresol, a benzyl alcohol, an alkyl paraben (methylparaben, ethylparaben, propylparaben, butylparaben, and the like), sodium dehydroacetate, an o-cresol, a p-cresol, a chlorocresol, a phenylmercuric nitrate, a thimerosal, a benzoic acid and any mixture thereof of one or more preservatives. See, e.g., Wallhauser, K., Develop. Biol. Standard. 24, pp. 9-28 (Basel, S. Krager, 1974. In some embodiments, the soft gelatin shells may contain a preservative to prevent the growth of fungi. In certain embodiments, preservatives may include the parabens, such as methylparaben, propylparaben, isopropylparaben, butylparaben, and isobutylparaben, and their salts such as sodium butylparaben, benzoic acid and its salts and esters, benzyl alcohol, urea derivatives such as diazofidinyl urea, imidazolidinyl urea, and DMDM hydantoin, sorbic acid and its salts, and the like. In various embodiments, the preservative may be absent.

The term "opacifier" refers to an agent or a mixture of agents which when added to a preparation make the ensuing system opaque. Representative opacifier agents include, but are not limited to, pharmaceutically acceptable metal oxides, especially titanium dioxide. Certain embodiments may include about 0.2 wt. % to about 1.2 wt. % of opacifier mixed with the plant-based component mass of the softgel. In some embodiments, the opacifier may be absent.

The term "flavorant" refers to a compound that provides a desired taste and/or smell. The flavorant can be a natural or artificial compound, and it can, but does not have to be, oil-soluble. Flavorants include isoamyl acetate (or other banana flavorant), benzaldehyde (or other almond flavorant), cinnamic aldehyde (or other cinnamon flavorant), citric acid or ethyl propionate (or other fruity flavorant), methyl anthranilate (or other grape flavorant), limonene (or other orange flavorant), ethyl decadienoate (or other pear flavorant), allyl hexanoate (or other pineapple flavorant), ethyl maltol (or other sugar or cotton candy flavorant), ethylvanillin (or other vanilla flavorant), methyl salicylate (or other wintergreen flavorant), glyceryl monoacetate (E1516 food additive), glyceryl diacetate (E1517 food additive), and combinations thereof. Some embodiments may include about 0.1 wt. % to about 2 wt. % of flavorant. The term "colorant" refers to compositions or compounds, such as, but not limited to, pigments, dyes and tints, which impart color. Typical colorants may include, carotenoids (E160, E161, E164), chlorophyllin (E140, E141), anthocyanins (E163), and betanin (E162). Other colorants such as, annatto (E160b), a reddish-orange dye made from the seed of the achiote, caramel coloring (E150a-d), made from caramelized sugar, carmine (E120), a red dye derived from the cochineal insect, Dactylopius coccus, elderberry juice (E163), lycopene (E160d), paprika (E160c), and turmeric (E100) may also be used.

The term "excipient" as used herein includes, but is not limited to, preservative, plasticizer, opacifier, colorant and flavorant as described above, or any combination thereof. The term excipient may also include a solvent, binder, surfactant, emulsifier, wetting agent, suspending agent, or any combination thereof. Suitable excipients or additives that can be used in the formulation of softgel capsules are described in, e.g., Lachman, et al., "The Theory and Practice of Industrial Pharmacy," 4th Edition (2013); Rowe et al., "Handbook of Pharmaceutical Excipients," 8th Edition (2017); and Remington, "The Science and Practice of Pharmacy," 22nd Edition (2015). From the regulatory perspectives, all excipients and additives used in the formulation of the softgel capsules described herein should preferably be approved for use in oral pharmaceutical dosage forms.

The softgel shell of the capsules is filled with the sleep composition. The sleep composition may be mixed, dissolved, dispersed, suspended, or emulsified with a liquid vehicle. The characteristics of the liquid vehicle may be hydrophilic or lipophilic. In certain embodiments, the liquid vehicle may include a combination of hydrophilic and lipophilic materials. In various embodiments, the hydrophilic materials, lipophilic materials, or combinations thereof, are encapsulated within the softgel shell in the form of a preconcentrate. In some embodiments, the preconcentrate further includes one or more surfactants. In certain embodiments, the ingredients of the liquid vehicle are present in the form of emulsions either before, during or after oral administration of the softgel capsules. In various embodiments, the emulsions include microemulsions, nanoemulsions and combinations thereof.

In some embodiments, the liquid vehicle may include one or more oils such as silicone oil, vegetable oil, glycerin, hydrogenated vegetable oil, lecithin, beeswax, tochopherols, polyethylene glycols (e.g., PEG 200, 300, 400 or 600), polyoxyethylene-polyoxypropylene copolymers (poloxamers), propylene glycol, triglycerides of medium chain fatty acids, omega oil, soybean oil, canola oil, sunflower oil, macadamia oil, peanut oil, grapeseed oil, pumpkin seed oil, linseed oil, flaxseed oil, olive oil, maize oil, safflower oil, sesame oil, pine kernel oil, conjugated linoleic acid, almond oil, peach kernel oil, apricot kernel oil, walnut oil, rapeseed oil, raspberry seed oil, bilberry seed oil, cranberry seed oil, pomegranate seed oil and other fruit seed oils, seabuckthorn oil, chia oil, perilla oil, diaglycerol (DAG) oil, vegetable derived sources of omega 3, fermented sources of eicosapentaenoic acid (EPA), fermented sources of docosahexaenoic acid (DHA), fermented sources of a combination of EPA, DHA and other omega 3s, including fish oil and hill oil, sources of gamma-linolenic acid (GLA) or stearidonic acid (SA), fractionated coconut oil, and combinations thereof. Sources of DHA, EPA and alpha-linoleic acid (ALA) include, but are not limited to, fish oils, yeasts or other microorganisms or monocellular sources and vegetable oils, primarily flaxseed, soy, and canola. Sources of GLA include, but are not limited to, evening primrose oil, blackcurrant seed oil, borage oil, and echium oil.

In view of the many possible embodiments to which the principles of the disclosed invention may be applied, it should be recognized that the illustrated embodiments are only preferred examples of the invention and should not be taken as limiting the scope of the invention.

What is claimed is:

1. A dosage unit comprising 1.5 mg to 4.0 mg melatonin, 50 mg to 275 mg valerian extract, 20 mg to 140 mg lemon balm extract, and 6.0 mg to 11.0 mg L-theanine, wherein the dosage unit is in the form of a softgel capsule for promoting sleep, wherein melatonin, valerian extract, lemon balm extract, and L-theanine are the only sleep inducing-active components of the dosage unit.

2. The dosage unit of claim 1, wherein the dosage unit comprises 100 mg to 200 mg valerian extract, and 50 mg to 120 mg lemon balm extract.

3. The dosage unit of claim 1, wherein the softgel capsule includes a shell and a fill composition, wherein the shell comprises at least one plant-based component, and the fill composition comprises the valerian extract, the lemon balm extract, the L-theanine, and the melatonin.

4. The dosage unit of claim 3, wherein the fill composition further comprises triglycerides of medium chain fatty acids.

5. The dosage unit of claim 1, wherein the combined amount of valerian extract, lemon balm extract, and L-theanine is 100 mg to 400 mg.

6. The dosage unit of claim 1, wherein the combined amount of valerian extract, lemon balm extract, and L-theanine is 150 mg to 300 mg.

7. A method comprising promoting sleep in an individual in need thereof, by orally administering to the individual the dosage unit of claim 1.

8. A method comprising promoting sleep in an individual in need thereof, by orally administering to the individual the dosage unit of claim 2.

* * * * *